United States Patent [19]

Scuri et al.

[11] Patent Number: 5,114,966
[45] Date of Patent: May 19, 1992

[54] 2,3-DIHYDRO-5-OXY-4,6,7-TRIMETHYL-BENZOFURANS 2-(RS)-SUBSTITUTED, USEFUL AS ANTIOXIDIZING PHARMACEUTICAL PRODUCTS HAVING MUCOREGULATING AND ANTI-ISCHEMIC PROPERTIES

[75] Inventors: Romolo Scuri, Frosinone; Mario Brufani, Castelgandolfo; Stefano Ceccarelli, Frosinone; Patrizia De Vellis, Frosinone; Patrizia Giannetti, Frosinone; Agnese Paesano, Frosinone; Sergio Zanarcella, Mentana, all of Italy

[73] Assignee: Biomedica Foscama Industria Chimico-Farmaceutica S.p.A., Rome, Italy

[21] Appl. No.: 562,731

[22] Filed: Aug. 6, 1990

[30] Foreign Application Priority Data

Aug. 18, 1989 [IT] Italy ................. 21532 A/89

[51] Int. Cl.$^5$ ............ A61K 31/34; C07D 307/79; C07D 307/80
[52] U.S. Cl. ............................ 514/469; 544/318; 548/186; 549/462; 549/470
[58] Field of Search ............. 549/462, 470; 548/186; 544/318; 514/274, 369, 469

[56] References Cited

U.S. PATENT DOCUMENTS 4,966,973 10/1990 Goto et al. ............ 549/462
4,999,350 3/1991 Brufani et al. ........ 549/462

Primary Examiner—Bernard Dentz
Attorney, Agent, or Firm—Notaro & Michalos

[57] ABSTRACT

The herein-described invention concerns new 2,3-dihydro-5-oxy-4,6,7-trimethylbenzofuranes 2-(RS)-substituted, the synthesis procedure and the relative therapeutic use as antioxidizing and radical-scavenging pharmaceuticals with mucoregulation and anti-ischemic properties.

6 Claims, No Drawings

2,3-DIHYDRO-5-OXY-4,6,7-TRIMETHYLBENZOFURANS 2-(RS)-SUBSTITUTED, USEFUL AS ANTIOXIDIZING PHARMACEUTICAL PRODUCTS HAVING MUCOREGULATING AND ANTI-ISCHEMIC PROPERTIES

FIELD OF THE INVENTION

It is known that free radicals and their oxidizing metabolites that are formed starting with oxygen can—under pathological conditions—damage various organs, such as the brain, the heart, and the respiratory system, and are also implicated in the pathogenesis of inflammatory processes, tumoral processes, platelet aggregation, and miocardiac and cerebral neurosis.

The oxidation damage caused by the oxygen metabolites can occur at the proteinic-structure and lipidic-structure levels of the tissues.

The phenomenon known as lipidic perioxidation is one of the major causes of cellular damage and can be effectively inhibited by anti-oxidizing and radical-scavenging substances, which can therefore actually stop the destruction of the cellular membranes. At the proteinic-structure level, the free oxygen radicals deactivate the alpha-1-protease inhibitor and thus contribute to the genesis of pulmonary emphysema and the amplification of respiratory-system inflammatory processes.

As concerns the central nervous system, the oxygen radicals are important mediators of the tissue damage that occurs during the reperfusion following cereal ischemia.

As concerns micardiac ischemia, the free oxygen radicals contribute to the cause of miocardiac damage both during the ischemia and during the postischemia riperfusion.

Antioxidizing and radical-scavenging substances neutralize the reactive oxygen metabolites and can therefore be useful therapeutic agents for the treatment of pulmonary emphysema and inflammatory processes involving the mucous membranes of the respiratory system, as well as for treating the after-effects of cerebral or cardiac infarction.

A few of the substances synthesized for achieving this end which are claimed in this invention have been shown to not only be very active as antioxidants and radical scavengers (particularly in vivo), but have also been seen to have outstanding mucolytic and mucoregulating properties, which permit brining the pathological tracheal-bronchial mucous back to the physiological condition, in particular as regards the regulation of the production, composition and rheology of mucous.

DETAILED DESCRIPTION OF THE INVENTION

The invention herein described concerns a substance which has a 2,3-dihydrobenzofuranic structure with the following formula (I):

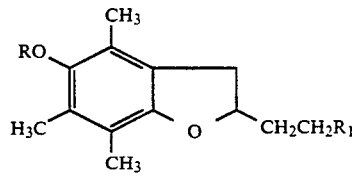

to their pharmaceutically-acceptable salts, in which:

R is
  a hydrogen;
  a linear or branched alkyl with 1–6 carbon atoms;
  a benzyl;
  a $-COR_2$ aliphatic acyl, where $R_2$ is a linear or branched alkyl with 0–6 carbon atoms;
  a hemiacyl of a bicarboxylic acid, in particular hemisuccinoyl;

$R_1$ is
  a hydrogen;
  an hydroxyl;
  a $-COOR_3$ acyloxy group, where $R_3$ is a lower alkyl, in particular methyl;
  a sulphydrylic group;
  a $-SR_4$ thioether, where $R_4$ is a heterocyclic residue, in particular 2-thiazolinic and 2-pyrimidinic;
  a $-SCOR_3$ acylthio group, where $R_3$ is as described before;
  a primary aminic group;
  a $-NR_5R_6$ dialkylaminic radical, where $R_5$ and $R_6$ are either lower alkyls or form a saturated hetercyclic ring, in particular piperidine, pyrrolidine, morpholine and N-methylpiperazine;
  a $-NHCOR_7$ secondary amide, where $R_7$ is a lower alkylic or an acrylic residue, in particular methyl and 3,4,5-trimethoxyphenyl;
  a halogen, in particular bromine and iodine.

The object of this invention also concerns the procedure for the preparation of the above-described new compounds. These are synthesized according to one of the two methods A and B described, respectively, in diagrams 1 and 2.

DIAGRAM 1

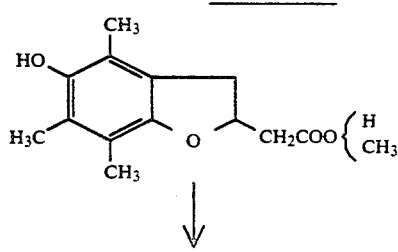

-continued
DIAGRAM 1
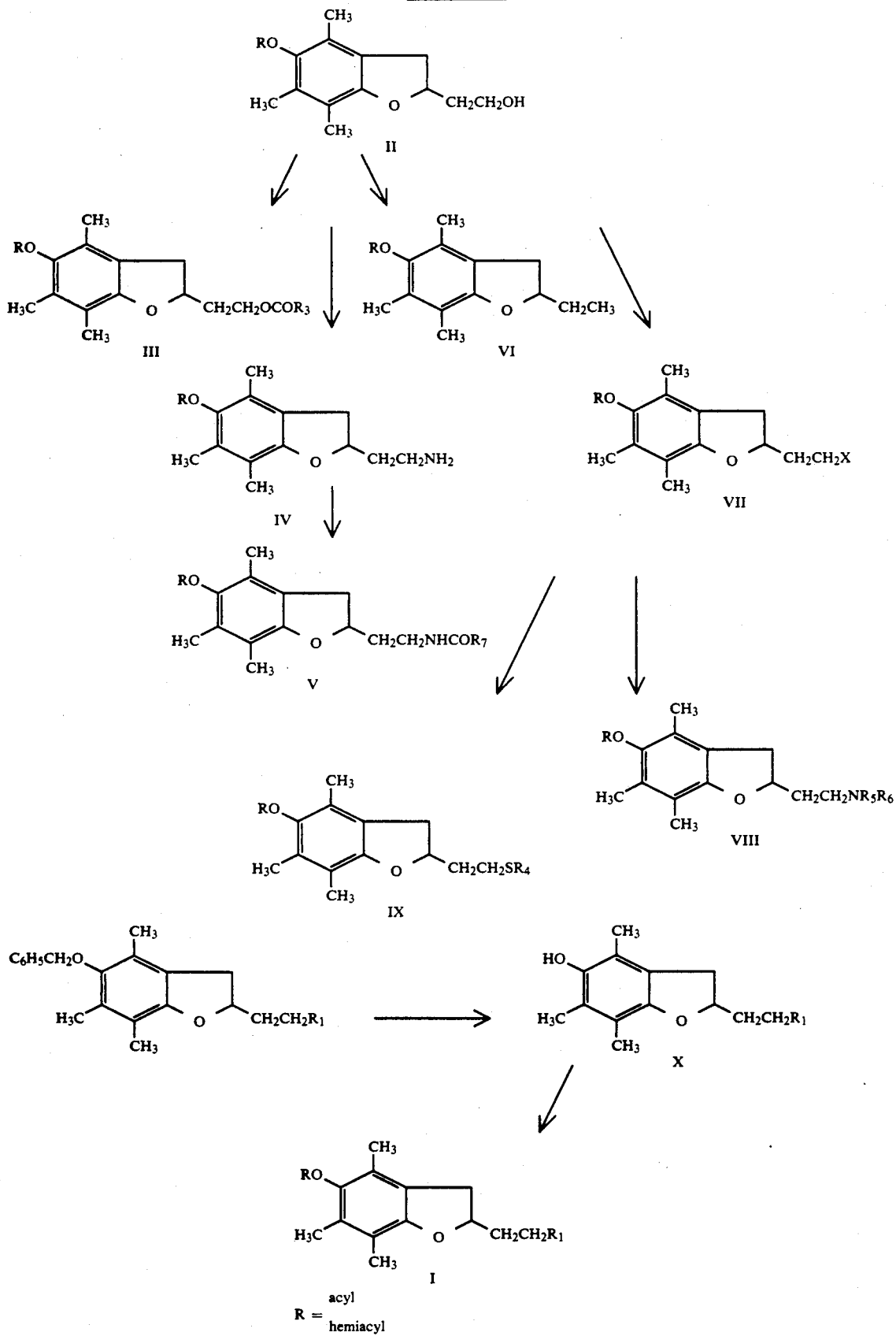

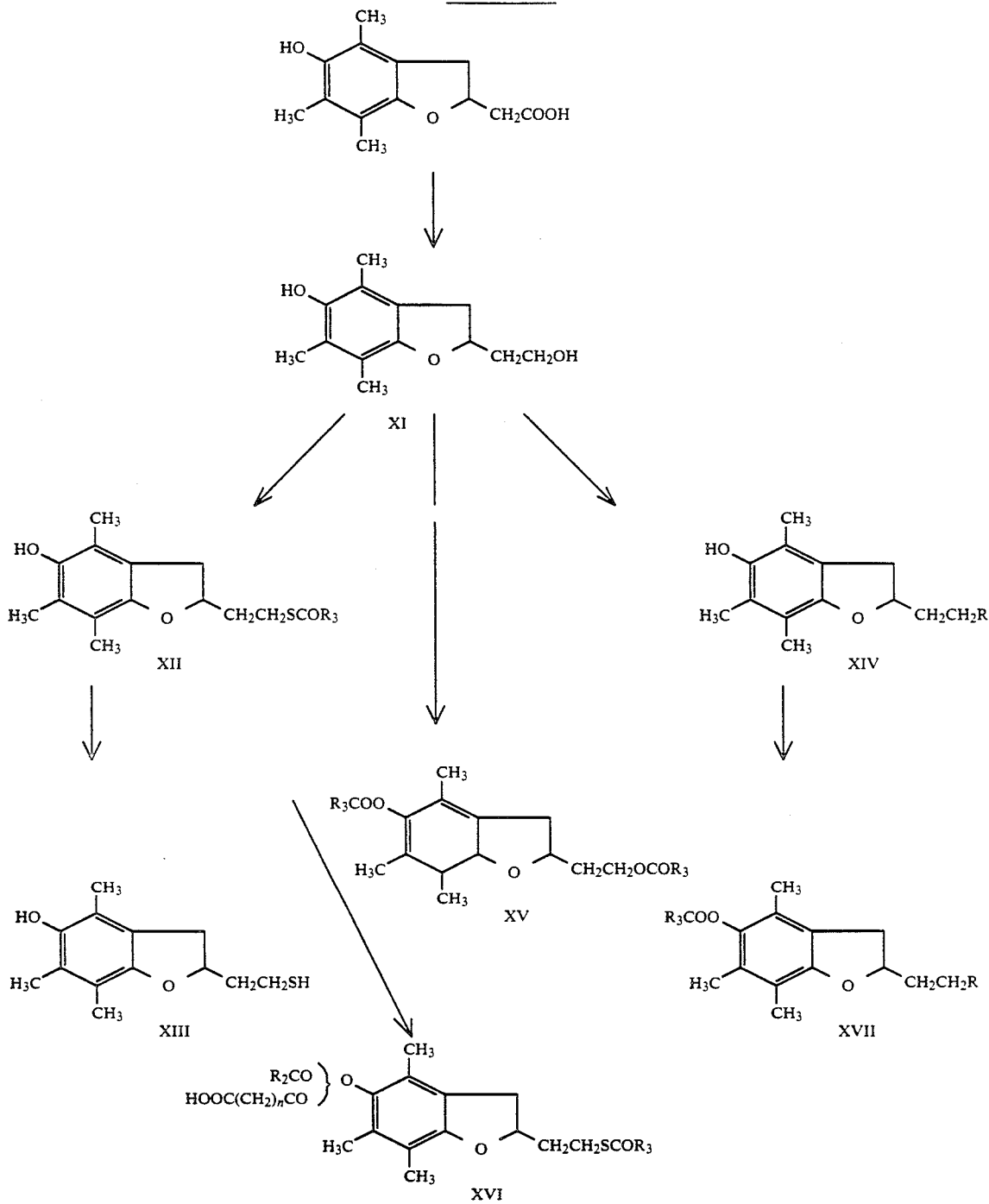

DIAGRAM 2

The substrata used in these cases 2-(RS)-(2,3-dihydro-5-hydroxy-4,6,7-trimethylbenzofuranyl)acetic acid or its methyl ester. These compounds are described and claimed in U.S. Pat. No. 4,999,350.

The synthetic method A calls for the alkylization of the phenolic hydroxyl in 5 position of the aforesaid acid (or its methyl ester) by treating with dialkyl sulfate or, in the case of benzylation, with a benzyl halide. On the other hand, the introduction of a branched alkyl is obtained by treating the methyl 2-(RS)-(2,3-dihydro-5-hydroxy-4,6,7-trimethylbenzofuranyl) acetate with the appropriate alcohol (for example, isopropanol), triphenylphosphine and dialkyl azodicarboxylate. The thus obtained phenolic ester is then treated with lithium and aluminum hydride (or some other appropriate compounds for reducing the carboxylic group, such as aluminum diisobutyl hydride or boron hydride) in solution with an inert organic solvent such as tetrahydrofurane or diethyl ether, to give the 2-(R)-(2-hydroxyethyl)-2,3-dihydro-5-alkoxy-4,6,7-trimethylbenzofurane (structure II). At this point, an appropriate substitution or functionalization reaction on the hydroxyl group can be performed, whereby the following compounds are obtained:

A1) structure III esters, obtained by treating alcohol of formula II with the appropriate anhydride of the acid (or the corresponding chloric acid chloride), under the usual alcohol acylation conditions;

A2) structure IV primary amines, obtained by treating the same alcohol II with phthalimide, triphenylphosphine, and dialkylazodicarboxylate, followed—after isolation of the N-substituted phthalimide—by reacting the hydrazine hydrate to free the primary amine;

A3) structure V secondary amides, obtained by treating the amines reference in par. A2 with an activated derivative of the appropriate $R_7COOH$ carboxylic acid, where $R_7$ is as previously described, in a aprotic organic solvent such as chloroform, and optionally in the presence of an organic base such as triethylamine;

A4) 2-(RS)-ethyl-2,3-dihydro-5-alcoxy-4,6,7-trimethylbenzofuranes of structure VI, obtained by treating alcohol II with p-toluenesulfonyl chloride (or other sulfonyl chloride such as trifluoromethansulfonyl chloride) under the usual sulfonate-formation conditions, and—after having isolated the sulfonic ester—by reaction this with a reducing agent such as lithium and aluminum hydride in an inert organic solvent such as tetrahydrofurane;

A5) structure VII halides, obtained by reacting compound II with halogen, triphenylphosphine and a nitrogenated hetercyclic base such as imidazol in a toluene solution or some other analogous solvent, or by treating the same alcohol II with an appropriate halogenating agent such as thionyl chloride or phosphorus tribromide;

A6) structure VIII tertiary amines (in which $R_5$ and $R_6$ are as previously described), obtained from the VII halide referenced in par. A5 by treating with the appropriate secondary amine $HNR_5R_6$;

A7) structure IX thioeters, obtained by treating the VII halide, reference in par. A5, with the appropriate thiol $R_4SH$, where $R_4$ is as previously described, in the presence of non-nucleophile bases such as bicycled 1,8-diazabicyclo-[5,4,0]undec-7ene in an inert solvent such as benzene.

When R is a benzyl, the above-described A1, A2, A3, A4 and A6 compounds can be de-protected by catalytic hydrogenation, thus producing structure X phenols which could also be acylated in the usual manner, thus finally obtaining structure I compounds where R is an acyl or hemiacyl of bicarboxylic acid.

The second series of compounds claimed with this invention is prepared by following the synthetic method B (Diagram 2). In this case, reduction of the carboxylic group is obtained by directly treating 2-(RS)-(2,3-dihydro-5-hydroxy-4,5,7-trimethylbenzofuranyl)acetic acid (IRFI 005) with lithium and aluminum hydride (or a suitable reducing agent such as aluminum diisobutyl hydride or boron hydride in solution with an inert organic solvent such as tetrahydrofurane or diethyl ether, thus obtaining the compound 2-(RS)-(2-hydroxyethyl)-2,3-dihydro-5-hydroxy-4,6,7 -trimethylbenzofurane (IRFI 039, XI), the key intermediate for the subsequent functionalization of the molecular. In fact, this compound gives:

B1) structure XII thioesters, obtained by reacting with triphenylphosphine, dialkyl azodicarboxylate and the appropriate thioacid in an inert solvent such as tetrahydrofurane; the thiol of formula XII can also be obtained by alkaline hydrolysis in mild condition (typically by means of diluted ammonia);

B2) structure XII iodide (IRFI 066), obtained by treating the XI with iodide, triphenylphosphine, and an azotated heterocyclic base such as imidazol in a toluene solution or another analogous solvent;

B3) diacylderivatives of formula XV, obtained by treating the alcohol of formula XI with the suitable chloride or anhydride of the acid under standard esterification conditions.

The products described in B1 and B2 can be subsequently actylated to phenolic oxydryl in 5 position, this obtaining compound of formula XVI and XVII structures, respectively. In particular, by treating compound XII—where $R_3 = CH_3$ (IRFI 061)—with succinic anhydride in a pyridine solution at the pyridine reflux temperature in an inert atmosphere, the hemisuccinate of 5-[2-(RS)-(2-acetylthioethyl)-2,3-dihydro-4,6,7-trimethylbenzofuranyl] (IRFI 042, structure I, where $R = HO_2CCH_2CH_2CO-$ and $R_1 = -SCOCH_3$) is obtained which has been shown to have outstanding mucoregulating properties, as well as considerable radical-scavenging activity in vivo.

The invention also concerns the use of the formula I substances as mucolytic and mucoregulating pharmaceuticals.

For example, Table I shows the effects on mucoproduction in mica by the compounds: 2-(RS)-(2-hydroxyethyl)-2,3-dihydro-5-hydroxy-4,6,7-trimethylbenzofurane [IRFI 039], hemisuccinate of 2-(RS)-(2 -acetylthidil-2,3-dihydro-4,6,7-trimethyl-5-benzofuranyl [IRFI 042] 2-(RS)-(2-acetylthioethyl)-2,3-dihydro-5-hydroxy-4,6,7-trimethylbenofurane [IRFI 061] and 2-(RS)-(2-iodoethyl)-2,3-hydroxy-5-hydroxy-4,6,7-trimethylbenzofuranyl [IRFI 066].

Table II shows the effects of compounds IRFI 039 and IRFI 042 on mucoproduction in rabbits.

Table III shows the effects of compound IRFI 042 on the ciliar motility of the tracheo-bronchial hepitelium in pidgeons.

Table IV shows the results relative to the dosages of lipoperoxides in rat liver homogenate after the administration of compound IRFI 042 and carbon tetrachloride intoxication. Table V shows the effects of compound IRFI 042 on gastroprotection after lesions induced by ethanol.

TABLE I: MUCORPRODUCTION IN MICE

The method described by Graziani et al. (Il Farmaco, Ed. Pr. 36, 167, 1981) was followed with appropriate modifications. Male albino CD 1 (Charles River) mice weighing between 22 and 24 g were used. Red phenol was dosed and injected intraperitoneally in the bronchial wash liquid, and the values obtained with the treated animals were compared with those obtained with the control animals. The pharmaceuticals were orally administered (gastric probe). Several of the best known mucolytic/mucoregulation agents used in human therapy were chosen as comparison drugs.

TABLE I

| | Oral administration (n = 10) | |
|---|---|---|
| SUBSTANCE | $DE_{50}$ (mg/kg) | 95% FIDUCIAL LIMITS |
| IRFI 039 | 80.426 | 66.667–94.184 |
| IRFI 042 | 65.696 | 56.444–74.948 |
| IRFI 061 | 203.148 | 125.670–280.626 |
| IRFI 066 | 154.215 | 131.568–176.863 |
| N-ACETYLCYSTEINE | 89.567 | 84.558–94.575 |
| BROMHEXINE | 177.062 | 170.872–183.252 |

TABLE I-continued

| | Oral administration (n = 10) | |
|---|---|---|
| SUBSTANCE | DE$_{50}$ (mg/kg) | 95% FIDUCIAL LIMITS |
| THIOPRONINE | 155.754 | 134.989–176.518 |

TABLE II: MUCORPRODUCTION IN RABBITS

The Scuri et al. method was used (Pharm. Chem. Bull. 119, 191, 1980), with male HY (Charles River) rabbits weighing 3–3.5 kg. The drugs were administered intravenously (auricular vein), and the tracheo-bronchial mucous was collected for a period of 4 hours before (basal) and after pharmacological treatment. The comparison drugs used were selected from some of the best known mucolytic/mucoregulation agents used for human therapy.

TABLE II

| | Endovenous administration (n = 10). | |
|---|---|---|
| SUBSTANCE | DE$_{50}$ (mg/kg) | 95% FIDUCIAL LIMITS |
| IRFI 039 | 4.203 | 3.780–4.672 |
| IRFI 042 | 1.546 | 1.524–1.567 |
| N-ACETYLCYSTEINE | 17.279 | 16.990–17.568 |
| SOBREROL | 7.541 | 7.520–7.563 |
| AMBROXOL | 6.358 | 4.197–8.518 |
| BROMHEXINE | 8.395 | 8.301–8.450 |

TABLE III: MUCOCILIAR CLEARANCE IN PIDGEONS

The study of the ciliar motility of the tracheo-bronchial epithelium was conducted by carrying out the Kubo et al. method (Arzneim. Forsch. 25, 1028, 1975), appropriately modified. Both male and female white King pidgeons weighing 500–700 g were used (Morini, S. Paolo d'Enza).

After exposing the tracheae of the animals, the tracheal mucosa was evidenced by making a longitudinal incision in the trachea. Very fine vegetable-carbon particles were applied to the mucosa and the length of time required for the particles to travel a certain distance was measured. After the drug under consideration was administered, the distances travelled by the carbon particles was noted every 5 minutes for a total period of one hour. These data were compared to those obtained prior to the treatment.

TABLE III

| | Endovenous administration (n = 3). | |
|---|---|---|
| SUBSTANCE | DOSE (mg/kg) | % CILIAR MOTL. VAR. (X) +/− ES |
| IRFI 042 | 31.25 | +15.3 +/− 4.74 |
| N-ACETYLCYSTEINE | 62.50 | +35.4 +/− 4.10 |
| AMBROXOL | 62.50 | +20.5 +/− 0.52 |
| HOMOCYSTEINE | 62.50 | +19.5 +/− 1.79 |

TABLE IV: ACTIVITY ON LIPOPEROXIDATION

The protective action of the tested substance on the toxicity produced by carbon tetrachloride was evidenced by means of doses of lipoperoxides applied to rat liver homogenate. These doses particularly evidenced the antioxidizing/radical-scavenging activity of the molecule under examination. Male Wistar (Charles River) rats weighing 100–200 g were used.

The substances being studied were administered one-half of one hour before intoxication with $CCl_4$ + liquid paraffin 1:1 (2.5 mg/kg orally administered). The animals were sacrificed 4 hours after intoxication, and their livers removed and homogenized. The lipoperoxides were dosed onto the homogenate using the thiobarbituric acid and malondialdehyde method, which were appropriately modified (Mirano et al., J. Chromatogr. 417, 371, 1987; Ohkawa et al., Anal. Biochem. 95, 357, 1979; Wong et al., Clin. Chem. 33, 214, 1987). The percent variation with respect to the animals not treated with the drug was then calculated.

TABLE IV

| | Oral administration (n = 5). | |
|---|---|---|
| SUBSTANCE | DOSE (mg/kg) | % VARIATION |
| IRFI 042 | 400 | −78 |
| BHT | 400 | −48 |
| α-TOCOFEROL | 100 | −74 |

TABLE V: GASTRIC LESIONS WITH ETHYL ALCOHOL

The protective action of the substances under study on gastric lesions induced by ethanol was tested by using the method described by Salim et al. (J. Pharm. Pharmacol. 39, 553, 1987). Male albino Charles River rats weighing 120–150 gr. were used. The animals were put in metabolic cages for 48 hours before testing without being fed, after which the drug was administered orally, followed one-half hour later by an oral administration of 40% ethyl alcohol (1 ml/rat), which caused gastric lesions. One hour after the ulcerogenic treatment, the animals were sacrificed, their stomachs removed, and the number of ulcers recorded. The percentage was then calculated between the treated and untreated animals.

TABLE V

| | Oral administration (n = 5). | |
|---|---|---|
| SUBSTANCE | DE$_{50}$ (mg/kg) | 95% FIDUCIAL LIMIT |
| IRFI | 45.352 | 40.459–50.838 |
| BHT | 106.026 | 33.549–245.603 |
| α-TOCOFEROL | >500 | |

Therefore, according to this invention, the compounds of formula I can be used as mucoregulation drugs for treating all respiratory-tract illnesses that are characterized by an increase in the secretion consistency and quantity (bronchitis, bronchiolitis, chronic bronchitis, bronchiolectasis and complications arising from asthma and pulmonary emphysema, pharyngopharyngitis and acute and chronic tracheitis, rhinitis and sinusitis) with the presence of phlogosis of the respiratory-tract mucosa.

Therapeutic administration of the formula I compounds can be done orally, topically, parenterally, and by inhalation or through the rectum in formulations containing standard, non-toxic pharmaceutical excipients. The term "parenterally" herein used refers to administration by subcutaneous, endovenous, intramuscular or intrasternal injection or technical infusions. The pharmaceutical compositions containing the active principles can be in any form which is suitable for oral administration, such as pills, water or oil suspensions, dispersable powders or granules, hard or soft capsules, syrups or elixirs. The compositions used for oral administration can contain one or more sweeteners or various agents for providing colour and aroma, as well preservatives, all of which for the purpose of rendering the pharmaceutical composition more appealing to the eye and the palate.

The formulations for oral administration include pills in which the active principle is mixed with non-toxic, pharmaceutically-acceptable excipients. The excipients can be inert diluents, such as calcium carbonate, sodium carbonate, lactose, calcium phosphate or sodium phosphate, granulating or disintegrating agents such as wheat starch or alginic acid; bonding agents such as starch, gelaine; lubricating agents such as magnesium stearate, stearic acid or talcum.

The pills can be either non-coated or coated by means of known techniques to retard the rate at which the substance is disintegrated and absorbed in the gastrointestinal tract, thus providing longer-lasting action.

The aqueous suspensions generally contain a mixture of the active principles and appropriate excipients. The excipients can be suspending agents, such as sodium carboxymethylcellulose, methylcellulose, hydroxypropylmethylcellulose, sodium alginate, polyvinylpyrrolidone; and dispersing or wetting agents. Furthermore, they can also contain one or more preservatives, preservants, such as ethyl or n-propyl p-hydroxybenzoate; one or more coloring agents; one or more aromatizing agents; and one or more sweetening agents.

The oily suspensions can be formulated by suspending the active principle in a vegetable or mineral oil. These suspensions can contain sweetening or aromatizing agents to make the preparation more pleasant-tasting.

The dispersable powders and granules that are suitable for preparing a aqueous suspension by adding water contain a mixture of the active principle with a dispersing or wetting agent, a suspending agent, and one or more preserving agents.

The pharmaceutical compositions of this invention can also be in the water-oil emulsion form. The oily phase can be substituted by a vegetable or mineral oil. The emulsifying agents can be natural rubbers such as acacia rubber, or natural phosphatides such as lecitine or natural or synthetic fatty acid esters.

The syrups and elixirs can be formulated with sweetening agents such as glycerol, sorbitol or saccharose. The pharmaceutical compositions can be in the form of sterile, injectable aqueous or oily suspensions, which can be formulated using known techniques and dispersing or wetting agents, as well as known suspending agents. The sterile, injectable preparations can be sterile, injectable solutions or suspensions in a non-toxic solvent or diluent which is suitable for parenteral use.

The formula I compounds can also rectally administered via the rectum in the form of suppositories. These compositions can be prepared by mixing the active principle with a suitable non-irritating excipient which is in the solid state at room temperature but becomes a liquid at rectal temperature. It thus melts inside the rectum and releases the drug. Polyethylenglycols and cocoa butter are suitable for making these suppositories. Various creams, unguents, gelatins, solutions, suspensions and other appropriate formulations containing the mucolytic compound can be prepared for topical use.

The following examples illustrate the invention without, however, imposing limitations.

EXAMPLE 1

2-(RS)-(2-hydroxyethyl)-2,3-dihydro-5-benzyloxy-4,6,7-trimethylbenzofurane (IRFI 072)

A solution of methyl 2-(RS)-(2,3-dihydro-5-hydroxy-4,6,7-trimethylbenzofuranyl) acetate (38.5 g, see Italian Patent Application No. 21603 A/88) in 350 ml of dimethylformamide is added to 42.5 g of potassium carbonate and 35.5 ml of benzyl chloride. The mixture is agitated under a vacuum at room temperature for 48 hours. When the reaction is complete, water is added and extraction with ethyl acetate is performed. The extracts are washed with water, dried and evaporated under vacuum. The raw residue is purified by column chromatography ($SiO_2$), obtaining 37.7 g of a white solid. IR (KBr): 1731 cm$^{-1}$ ($\nu COOCH_3$) $^1$H-NMR ($CDCl_3$): δ 7.5–7.2 (5H,m), 5.3–3.8 (1H,m), 4.7 (2H,s), 3.7. (3H,s), 3.3–2.6 (4H,m), 2.2 (6H,s), 2.1 (3H,s).

The obtained methyl 2-(RS)-(2,3-dihydro-5-benzyloxy-4,6,7-trimethylbenzofuranyl) acetate is solubilized in 250 ml of anhydrous tetrahydrofurane anhydride and added to a suspension of 23 gr. of lithium aluminum hydride in 90 ml of anhydrous tetrahydrofurane. The mixture is then agitated in an inert atmosphere for 30 minutes, after which the excess of hydride is destroyed by gradually adding 1 N hydrochloric acid. The inorganic hydroxides are then filtered and suspended in ethylic ether for about 15 minutes, after which the filtrates are put together, dried and evaporated in a solvent under a vacuum. 33.5 g of raw product and that is crystallized from hexane. m.p. 94° C., IR (KBr): 3342 cm$^{-1}$ ($\nu OH$); $^1$H-NMR ($CCl_4$): δ7.5–7.2 (5H,m), 5.1–4.6 (1H,m), 4.7 (2H,s), 3.8 (2H,t), 3.3–2.6 (2H,m), 2.5 (1H,s), 2.15 (6H,s), 2.1 (3H,s), 2.0–1.8 (2H,m).

| Elementary analysis for $C_{20}H_{24}O_3$ (P.M. 312.41): | | |
|---|---|---|
| | % C | % H |
| Calc. | 76.89 | 7.74 |
| Found | 77.22 | 7.82 |

EXAMPLE 2

2-(RS)-(2-hydroxyethyl)-2,3 dihydro-5-methoxy-4,6,7-trimethylbenzofurane 4.0 gr. 2-(RS)-(2,3-dihydro-5-hydroxy-4,6,7-trimethylbenzofurane) acetic acid are solubilized in 16 ml of ethyl alcohol. Various portions of 1.8 ml of dimethyl sulfate are alternatively added to a solution of 1.5 g of sodium hydroxide in 4.8 ml of water. Finally, alkalizing is done with a solution of 208 mg of sodium hydroxide in 1.6 ml of water. The mixture is kept in reflux in an inert atmosphere for 4 hours. After cooling, the solution is acidified and extraction is performed. The organic phase if finally dried and evaporated 5.0 g of raw residue is obtained that is purified by chromatography ($SiO_2$).

2-(RS)-(2,3-dihydro-5-methoxy-4,6,7-trimethylbenzofuranyl) acetic acid thus obtained is reduced to alcohol by following the same procedure described in example 1, which produces a white solid. m.p. 74°–76° C.; IR (KBr): 3382 ($\nu OH$), 1239 cm$^{-1}$ ($\nu C-O-C$); $^1$H-NMR ($CCl_4$): δ5.0–4.5 (1H,m), 4.4 (1H,s), 3.7 (2H,t), 3.5 (3H,s), 3.3–2.4 (2H,m), 2.05 (6H,s), 2.0 (3H,s), 2.0–1.8 (2H,m).

Elementary analysis for $C_{14}H_{20}O_3$ (Molecular Weight 236.31)

|       | % C   | % H  |
|-------|-------|------|
| Calc. | 71.16 | 8.53 |
| Found | 71.06 | 8.65 |

2-(RS)-(2-hydroxyethyl)-2,3-dihydro-5-isopropyloxy-4,6,7-trimethylbenzofurane A solution of 5.9 ml of diisopropyl azodicarboxylate in 2 ml of dichloromethane is added, dropwise, to a mixture of 5.0 g of methyl 2-(RS)-(2,3-dihydro-5-hydroxy-4,6,7-trimethylbenzofuranyl) acetate, 2.3 ml of isopropanol and 7.8 g of triphenylphosphine in 80 ml of dichloromethane. The mixture is stirred all night long in a nitrogen atmosphere and at room temperature. The solvent is evaporated, and the residue is purifed by column ($SiO_2$) to obtain 4.2 g of methyl 2-(RS)-(2,3-dihydro-5-isopropyloxy-4,6,7-trimethylbenzofuranyl) acetate.

The ester thus obtained is reduced to alcohol by using the procedure described in example 1. 3.2 g of product are obtained. m.p. 80°-82° C.; IR(KBr): 3368 cm$^{-1}$ ($\nu$OH); $^1$H-NMR (CCl$_4$): $\delta$5.0–4.5 (1H,m), 4.4 (1H,s), 4.1–3.4 (3H,m), 3.3–2.5 (2H,m), 2.1 (6H,s), 2.0 (3H,s), 2.0–1.8 (2H,m), 1.3 (6H,d).

Elementary analysis for $C_{16}H_{24}O_3$ (Molecular Weight 264.36):

|       | % C   | % H  |
|-------|-------|------|
| Calc. | 72.69 | 9.15 |
| Found | 72.62 | 9.14 |

2-(RS)-(2-acetoxyethyl)-2,3-dihydro-5-benzyloxy-4,6,7-trimethylbenzofurane

A solution of 150 mg of 2-(RS)-(2-hydroxyethyl)-2,3-dihydro-5-benzyloxy-4,6,7-trimethylbenzofurane in 0.6 ml of pyridine is treated with 0.3 ml of acetic anhydride. The mixture is stirred in nitrogen atmosphere at room temperature for 6 hours. After acidifying with hydrochloric acid, the suspension is extracted with ethylic ether then the extracts are dried and evaporated 165 mg of a white crystalline solid are obtained. m.p. 80°-82° C.; IR(KBr): 1742 cm$^{-1}$ ($\nu$AcO); $^1$H-NMR (CCl$_4$): $\delta$7.4–7.1 (5H,m), 5.0–4.6 (1H,m), 4.6 (2H,s), 4.2 (2H,t), 3.4–2.6 (2H,m), 2.2 (3H,s), 2.1 (3H,s), 2.0 (6H,s), 2.0–1.8 (2H,m).

Elementary analysis for $C_{22}H_{26}O_4$ (Molecular Weight 354.45):

|       | % C   | % H  |
|-------|-------|------|
| Calc. | 74.55 | 7.39 |
| Found | 74.51 | 7.43 |

EXAMPLE 5

2-(RS)-(2-aminoethyl)-2,3-dihydro-5-benzoxy-4,6,7-trimethylbenzofurane hydrochloride 5.7 ml of diisopropyl azodicarboxylate is added, dropwise, to a mixture of 6.0 g of 2-(RS)-(2-hydroxyethyl)-2,3-dihydro-5-benzyloxy-4,6,7-trimethylbenzofurane cold to 0° C., 7.6 g of triphenylphosphine and 3.1 g of phthalimide in 35 ml of anhydrous tetrahydrofurane. After these additions, the mixture is brought to room temperature and stirred for 2 hours. After the solvent has been evaporated, the residue is purified with chromatography column ($SiO_2$), which produces 8.0 g of N-[2-(2,3-dihydro-5-benzyloxy-4,6,7-trimethyl-2-benzofuranyl)ethyl]phthalimide m.p. 108°-110° C.: IR(KBr): 1772, 1716 cm$^{-1}$ ($\nu$O=CNC=O). The phthalimide thus obtained is solubilized in a mixture of 50 ml of tetrahydrofurane and 20 ml of absolute ethanol. 3.2 ml of hydrated hydrazine are added dropwise and the mixture is kept under reflux with stirring for 2 hours. After the mixture has been brought to room temperature the formed phthalhydrazine is filtered out, and the filtrate is concentrated to a volume of about 20 ml. The additional phthalhydrazine which forms is filtered out. After the solvent is evaporated from the filtrate, the residue is treated with ethylic ether saturated with HCL to obtain the precipitate of the hydrochloride of the product. The precipitate is filtered under a vacuum, which gives 4.0 g of a white solid. m.p. 192°-193° C.; IR (KBr): 3032 cm$^{-1}$ ($\nu$NH$_3$+); $^1$H-NMR (CD$_3$OD): $\delta$7.5–7.2 (5H,m), 4.7 (2H,s), 3.4–2.7 (4H,m), 2.4–2.2 (2H,m), 2.2 (6H,s), 2.1 (3H,s).

Elementary analysis for $C_{20}H_{26}ClNO_2$ (Molecular Weight 347.88):

|       | % C   | % H  | % N  |
|-------|-------|------|------|
| Calc. | 69.05 | 7.53 | 4.03 |
| Found | 69.00 | 7.43 | 4.25 |

EXAMPLE 6

N-[2-(2,3-dihydro-5-benzyloxy-4,6,7-trimethyl-2-(RS)-benzofuranyl)ethyl]acetamide The 2-(RS)-(2-aminoethyl)-2,3-dihydro-5-benzyloxy-4,6,7-trimethylbenzofurane is acetylated with the same procedure as described in example 4. A white solid is obtained m.p. 138°-139° C.; IR(KBr): 3285 ($\nu$NH), 1648 cm$^{-1}$ ($\nu$NHCO); $^1$H-NMR (CDCl$_3$): $\delta$7.5–7.2 (5H,m), 6.8 (1H,t), 5.1–4.7 (1H,m), 4.7 (2H,s), 3.8–3.5 (2H,m), 3.3–2.8 (2H,m), 2.2 (6H,s), 2.1 (3H,s), 2.0–1.8 (3H,s).

Elementary analysis for $C_{22}H_{27}NO_3$ (Molecular Weight 353.46):

|       | % C   | % H  | % N  |
|-------|-------|------|------|
| Calc. | 74.76 | 7.70 | 3.96 |
| Found | 74.83 | 7.60 | 3.91 |

EXAMPLE 7

N-[2-(2,3-dihydro-5-benzyloxy-4,6,7-trimethyl-2-(RS)-benzofuranyl)ethyl]-3,4,5-trimethoxybenzamide A solution of 2.86 g of 3,4,5-trimethoxybenzoyl chloride in 35 ml of chloroform is slowly added to a 3.85 g solution of 2-(RS)-(2-aminoethyl)-2,3-dihydro-5-benzyloxy-4,6,7-trimethyl-benzofurane in 35 ml of chloroform and 2.0 ml of triethylamine. After stirring for one hour at room temperature, 1 M hydrochloric acid is added and the organic phase is separated and washed in a sodium bicarbonate solution, dried and evaporated. 4.42 g of—a white solid are obtained that is purified by crystallization from ethanol/ethyl acetate. m.p. 171°-173° C. IR(KBr): 3271 ($\nu$N—H), 1684, 1545 cm$^{-1}$ ($\nu$CONH); $^1$H-NMR (CDCl$_3$): $\delta$7.4–7.2 (5H,m), 7.0 (2H,s), 6.8 (1H,t), 5.1–4.7 (1H,m), 4.7 (2H,s), 3.8 (9H,s), 3.8–3.4 (2H,m), 3.2–2.7 (2H,m), 2.2 (6H,s), 2.1 (3H,s), 2.1–1.8 (2H,m).

| Elementary analysis for $C_{30}H_{35}NO_6$ (Molecular Weight 505.61): | | | |
|---|---|---|---|
| | % C | % H | % N |
| Calc. | 71.27 | 6.98 | 2.77 |
| Found | 71.11 | 6.90 | 2.73 |

EXAMPLE 8

2-(RS)-ethyl-2,3-dihydro-5-benzyloxy-4,6,7-trimethylbenzofurane 105 mg of p-toluenesulfonyl chloride is added to a solution of 156 mg of 2-(RS)-(2-hydroxyethyl)-2,3-dihydro-5-benzyloxy-4,6,7 -trimethylbenzofurane in 0.5 ml cooled to 0° C. The reaction mixture is stirred for 3 hours, then it is acidified and extracted. The organic extracts are dried and evaporated, thus giving 185 mg of raw product, which is then purified with chromatography ($SiO_2$). 153 mg of p-toluenesulfonate of 2[2,3-dihydro-5-benzyloxy-4,6,7-trimethyl-2-(RS)benzofuranyl-]ethyl are obtained. IR (KBr): 1359, 1177 cm$^{-1}$ ($\nu SO_2$). The product thus obtained is then solubilized in 2 ml of anhydrous tetrahydrofurane and added to a suspension of 45 mg of lithium and aluminum hydride in 5 ml of anhydrous tetrahydrofurane. The reaction mixture is stirred in an inert atmosphere for 30 minutes. The reaction process is carried out using the same procedure described in example 1. 82 mg of a white solid are obtained. m.p. 65°-67° C. IR (KBr): 1595 ($\nu$C—C), 1237 cm$^{-1}$ ($\nu$C—O—C); $^1$H-NMR (CDCl$_3$): δ7.5–7.1 (5H,m), 4.8–4.4 (1H,m), 4.7 (2H,s), 3.3–2.5 (2H,m), 2.2 (6H,s), 2.1 (3H,s), 1.9–1.5 (2H,m), 1.0-(3H,t).

| Elementary analysis for $C_{20}H_{24}O_2$ (Molecular weight 296.41): | | |
|---|---|---|
| | % C | % H |
| Calc. | 81.04 | 8.16 |
| Found | 80.89 | 8.09 |

EXAMPLE 9

2-(RS)-(2-bromoethyl)-2,3-dihydro-5-benzyloxy-4,6,7-trimethylbenzofurane

A solution of 0.8 ml of bromine in 15 ml of toluene is added, dropwise, to a solution of 4.0 gr. of 2-(RS)-(2-hydroxyethyl)-2,3-dihydro-5-benzyloxy-4,6,7-trimethylbenzofurane, 5.1 g of triphenylphosphine and 1.3 gr of imidazol in 70 ml of toluene. The mixture is stirred at room temperature for 15 minutes, after which the imidazol*HBr is filtered out and the filtrate is evaporated. The residue is treated with ethylic ether to obtain a precipitate of triphenylphosphine oxide, which is filtered out. After the residue has been evaporated, the obtained 7.7 g of raw material is purified by means of the column chromatography (SiO$_2$), which produces 4.0 g of a yellow solid. m.p. 66°-68° C.; IR(KBr): 1549 ($\nu$C—C), 1075 cm$^{-1}$ ($\nu$C—O—C); $^1$H-NMR (CDCl$_3$): δ7.4–7.1 (5H,m), 5.0–4.5 (1H,m), 4.6 (2H,s), 3.5 (2H,t), 3.3–2.6 (2H,m), 2.3–2.1 (2H,m), 2.05 (9H,s).

| Elementary analysis for $C_{20}H_{23}BrO_2$ (Molecular weight 375.30): | | |
|---|---|---|
| | % C | % H |
| Calc. | 64.01 | 6.18 |

| Elementary analysis for $C_{20}H_{23}BrO_2$ (Molecular weight 375.30): | | |
|---|---|---|
| | % C | % H |
| Found | 64.36 | 6.47 |

EXAMPLE 10

2-(RS)-(2-diethylaminoethyl-2,3-dihydro-5-benzyloxy-4,6,7-trimethylbenzofurane hydrochloride A solution of 122 mg of 2-(RS)-(2-bromoethyl)-2,3-dihydro-5-benzyloxy-4,6,7-trimethylbenzofurane in 1 ml of diethylamine is made to reflux for 6 hours. After the excess diethylamine has evaporated, the residue is treated with a solution of sodium bicarbonate and extracted with ethyl. The extract are washed with water, dried and evaporated. The residue is treated with ethyl ether saturated with hydrochloric acid, which precipitates the hydrochloride product 100 mg of a white solid are obtained. m.p. 164°-166° C.; IR (KBr): 2646, 2442 ($\nu$NH+), 1079 cm$^{-1}$ ($\nu$C—O—C); $^1$H-NMR (CDCl$_3$): δ7.5–7.2 (5H,m), 5.1–4.7 (1H,m), 4.7 (2H,s), 3.5–2.7 (8H,m), 2.5–2.3 (2H,m), 2.2 (6H,s), 2.1 (3H,s), 1.4 (6H,t).

| Elementary analysis for $C_{24}H_{34}ClNO_2$ (Molecular weight 403.99). | | | |
|---|---|---|---|
| | % C | % H | % N |
| Calc. | 71.35 | 8.48 | 3.47 |
| Found | 71.04 | 8.16 | 3.18 |

EXAMPLE 11

2-(RS)-[2-(4-morpholine)ethyl]-2,3-dihydro-5-benzyloxy-4,6,7-trimethylbenzofurane hydrochloride 6.37 g of 2-(RS)-(2-bromoethyl)-2,3-dihydro-4,6,7-trimethylbenzofurane are warm solubilized in 100 ml of absolute ethanol.

A solution of 3.2 ml of morpholine in 7 ml of absolute ethanol are then added, dropwise. The mixture is refluxed under stirring for 10 hours. After the solvent has evaporated, the residue is treated with 30 ml of saturated sodium bicarbonate solution. Ethylic ether is used to extract, and the extracts are washed twice with water, dried and evaporated. Ethylic ether saturated with HCL is used to treat the residue obtaining the precipitation of the hydrochloride product that—is then filtered under a vacuum to obtain 5.05 g of a white solid. m.p. 196°-198° C.; IR(KBr): 2600 cm$^{-1}$ ($\nu$NH+); $^1$H-NMR (CDCl$_3$): δ7.5–7.2 (5H,s), 5.1–4.5 (1H, m), 4.7 (2H,s), 4.3–4.8 (4H,m), 3.5–2.6 (8H,m), 2.4–2.2 (2H,m), 2.2 (6H,s), 2.1 (3H,s).

| Elementary analysis for $C_{24}H_{32}ClNO_3$ (Molecular weight 417.97): | | | |
|---|---|---|---|
| | % C | % H | % N |
| Calc. | 68.97 | 7.72 | 3.35 |
| Found | 68.49 | 7.63 | 3.09 |

EXAMPLE 12

2-(RS)-[2-(4-methyl-1-piperazine)ethyl)]-2,3-dihydro-5-benzyloxy-4,6,7-trimethylbenzofurane 2.5 g of 2-(RS)-(2-bromoethyl)-2,3-dihydro-5-benzyloxy-4,6,7-trimethylbenzofurane are warm solubilized in 80 ml of absolute ethanol. Then 1.7 ml of 1-methylpiperazine is added, dropwise, and the solution stirred with reflux for 8 hours. After the solvent has evaporated, the residue is treated with 20 ml of saturated sodium bicarbonate solution and extraction is made with ethylic ether. The organic extracts are washed twice with water, dried then and evaporated. After purification with chromatography ($SiO_2$) of the raw reaction material, 2.2 g of a white solid are obtained. m.p. 68°–71° C.; IR(KBr): 1456 cm$^{-1}$ ($\delta_s CH_2$); $^1$H-NMR (CDCl$_3$): δ7.5–7.2 (5H,m), 5.1–4.5 (1H,m), 4.7 (2H,s), 3.4–2.7 (2H,m), 2.7 –2.3 (10H,m), 2.25 (3H,s), 2.15 (6H,s), 2.1 (3H,s), 2.0–1.8 (2H,m).

| Elementary analysis for $C_{25}H_{34}N_2O_2$ (Molecular weight 394.56): | | | |
|---|---|---|---|
| | % C | % H | % N |
| Calc. | 76.10 | 8.69 | 7.10 |
| Found | 75.90 | 8.55 | 6.90 |

EXAMPLE 13

2-[2,3-dihydro-5-methoxy-4,6,7-trimethyl-b 2-(RS)-benzofuranyl]ethyl-2-thio-2-thiazoline hydrochloride (IRFI 074)

1.74 ml of 1,8-diazabicycle [5,4.0]undec-7ene(1,5-5) (DBU) and 2.91 g, of 2-(RS)-(2-bromoethyl)-2,3-dihydro-5-methoxy-4,6,7-trimethylbenzofurane are added successively to a solution of 1.28 g of 2-mercapto-2-thiaoline in 30 ml of benzene. The mixture is agitated for 2 hours at room temperature. After filtering the DBU*HBr, the filtrate is evaporated. The raw residue is purified by chromatography ($SiO_2$), 2.83 g of an oil is obtained which is salified by treating with HCL in ether. After filtration of the precipitate under vacuum 2.72 f. of a product is obtained. m.p. 169°–171° C. IR(KBr): 1570 ($\nu$C—C), 1084 cm$^{-1}$ ($\nu$C—O—C); $^1$H-NMR (CDCl$_3$): δ5.1–4.7 (1H,m), 4.4 (2H,t), 3.9–4.4 (4H,m), 3.6 (3H,s), 3.2–2.5 (2H,m), 2.3–2.1 (2H,m), 2.1 (6H,s), 2.0 (3H,s).

| Elementary analysis for $C_{17}H_{24}ClNO_2S_2$ (Molecular weight): | | | |
|---|---|---|---|
| | % C | % H | % N |
| Calc. | 62.03 | 7.57 | 3.29 |
| Found | 61.85 | 7.93 | 3.17 |

EXAMPLE 14

2-[(2,3-dihydro-5-methoxy-4,6,7-trimethyl-2-(RS)-benzofuranyl)ethylthio-2-pyrimidine 0.06 ml of DBU and a solution of 120 mg of 2-(RS)-(2-bromomethyl)-2,3-dihydro-5-methoxy-4,6,7-trimethylbenzofurane are successively added, to a solution of 40 mg of 2-mercaptopyrimidine in 1 ml of benzene. After stirring for 2 hours at room temperature, the DBU*HBr is filtered out and the filtrate is washed with water, dried and evaporated. The residue is purified by chromatography ($SiO_2$), and 112 mg of clear oil is obtained. IR (liquid film): 1080 cm$^{-1}$ ($\nu$C—O—C); $^1$H-NMR (CDCl$_3$): δ8.5 (2H,d), 6.9 (1H,t), 5.1–4.6 (1H,m), 3.8 (3H,s), 3.3 (2H,t), 3.2–2.6 (2H,m), 2.1 (6H,s), 2.05 (3H,s), 2.0–1.8 (2H,m).

| Elementary analysis for $C_{18}H_{22}N_2O_2S$ (Molecular weight 330.45): | | | |
|---|---|---|---|
| | % C | % H | % N |
| Calc. | 65.42 | 6.71 | 8.48 |
| Found | 65.35 | 6.67 | 8.45 |

EXAMPLE 15

2-(RS)-(2-acetoxyethyl)-2,3-dihydro-5-hydroxy-4,5,7-trimethylbenzofurane 150 mg palladium on 5% carbon is added to a solution of 1.8 g of 2-(RS)-(2-acetoxyethyl)-2,3-dihydro-5-benzyloxy-4,6,7-trimethylbenzofurane in 25 ml of absolute ethanol. The solution is kept under a hydrogen pressure of 50 psi for one hour at room temperature. After filtration of the catalyzer, on Celite, the solvent is evaporated, leaving 1.3 g of a white solid. m.p. 90°–92° C.; (IR)(KBr) 3389 ($\nu$OH), 1738 cm$^{-1}$ ($\nu$COCH$_3$); $^1$H-NMR (CDCl$_3$); δ5.1–4.6 (1H,m), 4.2 (2H,t), 3.3–2.7 (2H,m) 2.2 (3H,s), 2.05 (6H,s), 2.0 (3H,s), 2.0–1.8 (2H,m).

| Elementary analysis for $C_{15}H_{20}O_4$ (Molecular weight 264.32): | | |
|---|---|---|
| | % C | % H |
| Calc. | 68.16 | 7.63 |
| Found | 68.12 | 7.65 |

EXAMPLE 16

2-(RS)-(2-aminoethyl)-2,3-dihydro-5-hydroxy-4,6,7-trimethylbenzofurane hydrochloride The de-benzylization of the 2-(RS)-(2-aminoethyl)-2,3-dihydro-5-benzyloxy-4,6,7-trimethylbenzofurane hydrochloride is done with the same process as described in example 15. A white solid is obtained. m.p. 198°–199° C.; IR (KBr): 3410 ($\nu$OH), 3059 cm$^{-1}$ ($\nu$NH$_3$+); $^1$H-NMR (D$_2$O): δ3.4–2.7 (4H,m), 2.3–2.1 (2H,m), 2.1 (6H,s), 2.0 (3H,s).

| Elementary analysis for $C_{13}H_{20}ClNO_2$ (Molecular weight 257.76): | | | |
|---|---|---|---|
| | % C | % H | % N |
| Calc. | 60.58 | 7.82 | 5.43 |
| Found | 60.32 | 7.91 | 5.39 |

EXAMPLE 17

N-[2-(2,3-dihydro-5-hydroxy-4,6,7-trimethyl-2-(RS)-benzofuran)ethyl]acetamide

The de-benzylization of the N-[2-(2,3-dihydro-5-benzyloxy-4,6,7-trimethyl-2-(RS)-benzofuranyl) ethyl]acetamide is done with the same process as described in example 15. A white solid is obtained. m.p. 142°–145° C.; IR (KBr): 3387 ($\nu$OH), 1661 cm$^{-1}$ ($\nu$NHCO); $^1$H-NMR (CD$_3$OD): δ3.5–2.8 (4H,m), 2.1 (6H,s), 2.05 (3H,s), 2.0–1.8 (2H,m), 1.8 (3H,s).

Elementary analysis for $C_{15}H_{21}NO_3$
(Molecular weight 263.34):

|  | % C | % H | % N |
|---|---|---|---|
| Calc. | 68.41 | 8.04 | 5.32 |
| Found | 68.20 | 8.15 | 5.29 |

EXAMPLE 18

N-[2-(2,3-dihydro-5-hydroxy-4,6,7-trimethyl-2-(RS)-benzofuran)ethyl]-3,4,5-trimethoxybenzamide The de-benzylization of the N-[2-(2,3-dihydro-5-benzyloxy-4,6,7-trimethyl-2-(RS)-benzofuranyl) ethyl]-3,4,5-trimethyoxybenzamide is done by the following the procedure given in example 15. The obtained result is a white solid. m.p. 172°–174° C.; IR (KBr): 3399 ($\nu$OH), 1679 cm$^{-1}$ ($\nu$CONH); $^1$H-NMR (CD$_3$OD): $\delta$7.0 (2H,s), 3.8 (9H,s), 3.8–3.4 (2H,m), 3.3–2.7 (2H,m), 2.2 (6H,s), 2.1 (2H,m), 2.05 (3H,s).

Elementary analysis for $C_{23}H_{29}NO_6$
(Molecular weight 415.49):

|  | % C | % H | % N |
|---|---|---|---|
| Calc. | 66.49 | 7.03 | 3.37 |
| Found | 66.37 | 7.09 | 3.28 |

EXAMPLE 19

2-(RS)-ethyl-2,3-dihydro-5-hydroxy-4,6,7-trimethylbenzofurane

The de-benzylization of the 2-(RS)-ethyl-2,3-dihydro-5-benzyloxy-4,6,7-trimethylbenzofurane is done by following the procedure given in example 15. A white solid is obtained. m.p. 73°–75° C.; IR (KBr): 3378 cm$^{-1}$ ($\nu$OH); $^1$H-NMR (CDCl$_3$): $\delta$4.9–4.5 (1H,m), 4.2 (1H,s), 3.3–2.7 (2H,m), 2.1 (6H,s), 2.0 (3H,s), 1.8–1.5 (2H,m), 1.1 (3H,t).

Elementary analysis for $C_{13}H_{18}O_2$ (Molecular weight 206.28):

|  | % C | % H |
|---|---|---|
| Calc. | 75.69 | 8.79 |
| Found | 75.66 | 8.72 |

EXAMPLE 20

2-(RS)-(2-dimethylaminoethyl)-2,3-dihydro-5-hydroxy-4,6,7-trimethylbenzofurane hydrochloride The de-benzylation of the 2-(RS)-(2-dimethylaminoethyl)-2,3-dihydro-5-benzyloxy-4,6,7-trimethylbenzofurane hydrochloride is done by carrying out the procedure given in example 15. A white solid is obtained m.p. 171°–173° C.; IR (KBr): 3406 ($\nu$OH), 2651, 2438 cm$^{-1}$ ($\nu$NH+); $^1$H-NMR (CD$_3$OD); $\delta$3.5–2.7 (8H,m), 2.5–2.2 (2H,m), 2.1 (6H,s), 2.0 (3H,s), 1.4 (6H,t).

Elementary analysis for $C_{17}H_{28}ClNO_2$ (Molecular weight 313.87):

|  | % C | % H | % N |
|---|---|---|---|
| Calc. | 65.05 | 8.99 | 4.46 |
| Found | 64.89 | 9.08 | 4.40 |

EXAMPLE 21

2-(RS)-[2-(4-morpholine)ethyl]-2,3-dihydro-5-hydroxy-4,6,7-trimethylbenzofurane hydrochloride The de-benzylation of the 2-(RS)-[2-(4-morpholine)ethyl]-2,3-dihydro-5-benzyloxy-4,6,7-trimethylenzofurane is done with the procedure given in example 15. A white solid that can be salified with etherous HCl is obtained m.p. 205°–206° C.; IR (KBr): 3389 ($\nu$OH), 2612 cm$^{-1}$ ($\nu$NH+); $^1$H-NMR (CD$_3$OD): $\delta$4.3–3.8 (4H,m), 3.6–2.7 (8H,m), 2.5–2.2 (2H,m), 2.1 (6H,s), 2.0 (3H,s).

Elementary analysis for $C_{17}H_{26}ClNO_3$ (P.M. 327.85):

|  | % C | % H | % N |
|---|---|---|---|
| Calc. | 62.28 | 7.99 | 4.27 |
| Found | 62.08 | 8.08 | 4.19 |

EXAMPLE 22

2-(RS)-[2-(1-methyl-4-piperazine)ethyl]-2,3-dihydro-5-hydroxy-4,6,7-trimethylbenzofurane 2-(RS)-[2-(1-methyl-4-piperazine)ethyl]-2,3-dihydro-5-benzyloxy-4,6,7-trimethylbenzofurane is debenzylated by using the same procedure as described in example 15. A white solid is obtained. m.p. 76°–78° C.; IR (KBr): 3391 cm$^{-1}$ ($\nu$OH); $^1$H-NMR (CDCl$_3$): $\delta$5.1–4.5 (1H,m), 4.3 (1H,s), 3.5–2.7 (2H,m), 2.7–2.3 (10H,m), 2.25 (3H,s), 2.1 (6H,s), 2.05 (3H,s), 2.1–1.8 (2H,m).

Elementary analysis for $C_{18}H_{28}N_2O_2$ (Molecular weight 304.43):

|  | % C | % H | % N |
|---|---|---|---|
| Calc. | 71.02 | 9.27 | 9.20 |
| Found | 70.95 | 9.15 | 9.18 |

EXAMPLE 23

Butyric acid.
5-[2-(RS)-(2-acetoxyethyl-2,3-dihydro-4,6,7-trimethylbenzofuranyl]ester 0.7 ml of pyridine and 0.9 ml of butyryl hydrochloride are added dropwise to a solution of 2.0 g of 2-(RS)-(2-acetoxyethyl)-2,3-dihydro-5-hydroxy-4,6,7-trimethylbenzofurane in 8 ml of anhydrous tetrahydrofurane. After stirring for 1 hour at room temperature, the formed pyridine hydrochloride is filtered out. The filtrate is evaporated and treated with 1 N hydrochloric acid and extraction is done with diethyl ether. The extracts are dried and evaporated. The resulting residue is crystallized with benzene and provides 2.1 g of a white solid. m.p. 69°–71° C.; IR (KBr): 1729 ($\nu$COOR), 1756 cm$^{-1}$ ($\nu$COOAr); $^1$H-NMR (CDCl$_3$): $\delta$5.1–4.5 (1H,m), 4.2 (2H,t), 3.3–2.7 (2H,m), 2.4 (2H,t), 2.15 (6H,s), 2.1 (3H,s), 2.0–1.6 (4H,m), 1.1 (3H,t).

Elementary analysis for $C_{19}H_{26}O_5$
(Molecular weight 334.41):

|  | % C | % H |
|---|---|---|
| Calc. | 68.24 | 7.84 |
| Found | 68.23 | 7.86 |

EXAMPLE 24

Succinic acid, mono
[5-(2-(RS)-(2-acetamidoethyl)-2,3-dihydro-4,6,7-trimethylbenzofuranyl]ester A mixture of 2.6 g of N-[2-(2,3-dihydro-5-hydroxy-4,6,7-trimethyl-2-(RS)-benzofuranyl)ethyl]acetamide and 2.0 g of succinic anhydride in 15 ml of pyridine is refluxed in an inert atmosphere for 4 hours. After cooling, the resulting solution is acidified and extracted with ethyl acetate. After washing with water, the organic phase is re-extracted with an 8% sodium-bicarbonate solution. After the aqueous phase has been acidified, the obtained suspension is again extracted. The final extracts are dried and evaporated, and the residue is purified using a column chromatography ($SiO_2$ column). The result is 3.1 g of a white solid. m.p. 118°-20° C.; IR (KBr): 1751 ($\nu$COOAr), 1716 ($\nu$COOH), 1661 cm$^{-1}$ ($\nu$CONH); $^1$H-NMR (CDCl$_3$): $\delta$5.1-4.5 (1H,m), 3.7-2.6 (8H,m), 2.1 (6H,s), 2.0 (3H,s), 2.0-1.8 (2H,m), 1.8 (3H,s).

| Elementary analysis for $C_{19}H_{25}NO_6$ (Molecular weight 363.41): | | | |
|---|---|---|---|
| | % C | % H | % N |
| Calc. | 62.80 | 6.93 | 3.85 |
| Found | 62.73 | 6.96 | 3.85 |

EXAMPLE 25

2-(RS)-(2-hydroxyethyl)-2,3-dihydro-5-hydroxy-4,6,7-trimethylbenzofurane (IRFI 039)

2-(2,3-dihydro-5-hydro-5-hydroxy-4,6,7-trimethylbenzofurane) acid acetic (IRFI 005) is reduced to an alcohol by carrying out the procedure as described in example 1. The obtained raw product is crystallized with benzene. m.p. 123°-125°C.; IR (KBr): 3284 ($\nu$OH), 1005 cm$^{-1}$ ($\nu$C—O); $^1$H-NMR (CD$_3$OD): $\delta$5.1-4.4 (2H,m), 3.7 (2H,t), 3.3-2.6 (2H,m), 2.1 (6H,s), 2.0 (3H,s), 1.85 (2H,m).

| Elementary analysis for $C_{13}H_{18}O_3$ (Molecular weight 222.28): | | |
|---|---|---|
| | % C | % H |
| Calc. | 70.24 | 8.16 |
| Found | 69.99 | 8.23 |

EXAMPLE 26

2-(RS)-(2-acetylthioethyl)-2,3-dihydro-5-hydroxy-4,6,7-trimethylbenzofurane (IRFI 061)

A solution of 17.3 g of triphenylphosphine in 150 ml of anhydrous tetrahydrofurane is cooled to 0° C. After having agitated the mixture for one hour, 9.8 g of 2-(RS)-(2-hydroxyethyl)-2,3-dihydro-5-hydroxy-4,6,7-trimethylbenzofurane and 4.7 ml of thioacetic acid in 60 ml of tetrahydrofurane is added dropwise to 0° C. to the mixture. After an hour at 0° C. and 2 hours at room temperature, the mixture is evaporated under a vacuum, and the product is isolated by column chromatography ($SiO_2$). After crystallization from hexane, 10.7 g of a white crystalline solid is obtained. m.p. 89.5°-91.5° C.; IR (KBr): 3406 ($\nu$OH), 1686 cm$^{-1}$ ($\nu$SCOCH$_3$); $^1$H-NMR (CDCl$_3$): $\delta$5.1-4.5 (2H,m), 3.4-26.6 (4H,m), 2.3 (3H,s), 2.1 (9H,s), 1.9 (2H,m).

| Elementary Analysis for $C_{15}H_{20}O_3S$ (Molecular weight 280.38): | | |
|---|---|---|
| | % C | % H |
| Calc. | 64.26 | 7.19 |
| Found | 64.29 | 7.30 |

EXAMPLE 27

2-(RS)-(2-mercaptoethyl)-2,3-dihydro-5-hydroxy-4,6,7-trimethylbenzofurane

A solution of 5.1 g of 2-(RS)-(2-acetylthioethyl)-2,3-dihydro-5-hydroxy-4,6,7-trimethylbenzofurane in 90 ml of acetone is treated with 20 ml of a 25% $NH_3$ solution under nitrogen and stirred for 16 hours. After acidification, the mixture is extracted with ethyl acetate, and the extracts are dried and evaporated. The obtained 4.3 g of a white solid is obtained that can be crystallized with benzene. m.p. 163°-165° C.; IR (KBr): 3351 ($\nu$OH), 1237 cm$^{-1}$ ($\nu$Ar—O—CH); $^1$H-NMR (DMSO-d$_6$): $\delta$5.1-4.4 (1H,m), 3.5 (1H, sb), 3.2-2.6 (4H,m), 2.1 (2H,m), 2.0 (6H,s), 1.95 (3H,s), 1.2 (1H,m).

| Elementary Analysis for $C_{13}H_{18}O_2S$ (Molecular weight 238.34): | | |
|---|---|---|
| | % C | % H |
| Calc. | 65.51 | 7.61 |
| Found | 65.53 | 7.45 |

EXAMPLE 28

2-(RS)-(2-iodoethyl)-2,3-dihydro-5-hydroxy-4,6,7-trimethylbenzofurane (IRFI 066)

4.4 g of iodine are added to a mixture of 3.1 g of 2-(RS)-2-hydroxyethyl-2,3-dihydro-5-hydroxy-4,6,7-trimethylbenzofurane, 5.5 g of triphenylphosphine and 1.4 g of imidazol in 60 ml of toluene. The mixture is stirred for 3 hours at 60° C. The imidazole*HBr is then filtered out and the filtrate is evaporated. After purification by a column chromatography ($SiO_2$), 3.0 g of white solid are obtained. m.p. 96°-97° C.; IR (KBr): 3403 ($\nu$OH), 1195 cm$^{-1}$ (w CH$_2$I); $^1$H-NMR (CCl$_4$): $\delta$4.9-4.4 (1H,m), 4.0 (1H,s), 3.2 (2H,t), 3.0-2.5 (2H,m), 2.2 (2H,m), 2.1 (9H,s).

| Elementary analysis for $C_{13}H_{17}IO_2$ | | |
|---|---|---|
| | % C | % H |
| Calc. | 47.00 | 5.16 |
| Found | 46.98 | 5.14 |

EXAMPLE 29

2-(RS)-(2-acetoxyethyl)-2,3-dihydro-5-acetoxy-4,6,7-trimethylbenzofurane 2-(RS)-(2-hydroxyethyl)-2,3-dihydro-5-hydroxy-4,6,7-trimethylbenzofurane is acetylated using the procedure described in example 4. The obtained oil slowly crystallizes. IR (liquid film): 1758 ($\nu$AcOAr), 1741 cm$^{-1}$ ($\nu$AcOR); $^1$H-NMR (CCl$_4$): $\delta$5.0-4.5 (1H,m), 4.2 (2H,t), 3.4-2.7 (2H,m), 2.2 (3H,s), 2.1 (3H,s), 2.0 (6H,s), 1.9 (3H,s), 1.9-1.7 (2H,m).

Elementary analysis for $C_{17}H_{22}O_5$ (Molecular weight 306.36):

|       | % C   | % H  |
|-------|-------|------|
| Calc. | 66.65 | 7.24 |
| Found | 66.63 | 7.40 |

EXAMPLE 30

Succinic acid, mono 5-(2,3-dihydro-2,3-dihydro-2-(RS)-(2-acetylthioethyl)-4,6,7-trimethylbenzofurane) ester (IRFI 042)

A mixture of 11.4 g of 2-(RS)-(2-acetylthioethyl)-2,3-dihydro-5-hydroxy-4,6,7-trimethylbenzofurane and 8.1 g of succinic anhydride in 60 ml of pyridine is refluxed in a nitrogen atmosphere for 4 hours. After cooling, the resulting solution is acidified with HCl and extracted with ethyl acetate. The organic phase is washed with water and reextracted with an 8% $NaHCO_3$ solution. After acidification of the aqueous phase the product is again extracted with ethyl acetate. The extracts are dried and evaporated, and the raw residue is subjected to column chromatography ($SiO_2$). After crystallizing with $EtOH/H_2O$, 8.9 g of a white crystalline solid is obtained m.p. 102°-104° C.; IR (KBr): 1747 ($\nu RCOOAr$), 1710 ($\nu COOH$), 1693 cm$^{-1}$ ($\nu SCOCH_3$ H-NMR(CDCl$_3$): $\delta$5.1-4.5 (1H,m), 3.6-2.6 (8H,m), 2.3 (3H,s), 2.1 (3H,s), 1.95 (6H,s), 1.8 (2H,m).

Elementary analysis for $C_{19}H_{24}O_6S$ (Molecular weight 380.45):

|       | % C   | % H  |
|-------|-------|------|
| Calc. | 59.98 | 6.36 |
| Found | 59.99 | 6.37 |

EXAMPLE 31

2-(RS)-(2-iodoethyl)-2,3-dihydro-5-acetoxy-4,6,7-trimethylbenzofurane

The acetylation of the 2-(RS)-(2-iodoethyl)-2,3-dihydro-5-hydroxy-4,6,7-trimethylbenzofurane is done by carrying out the procedure as described in example 4. The obtained product is a white solid. m.p. 89°-90° C.; IR (KBr): 1748 cm$^{-1}$ ($\nu AcO$); $^1$H-NMR (CCl$_4$): $\delta$5.0-4.5 (1H,m), 3.2 (2H,t), 3.1-2.6 (2H,m), 2.3 (3H,s), 2.2-2.1 (2H,m), 2.1 (6H,s), 2.05 (3H,s).

Elementary analysis for $C_{15}H_{19}IO_3$ (Molecular weight 374.21):

|       | % C   | % H  |
|-------|-------|------|
| Calc. | 48.14 | 5.12 |
| Found | 48.18 | 5.08 |

We claim:

1. A compound of formula

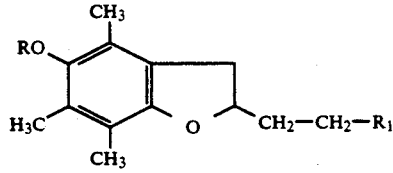

wherein R is:
a hydrogen atom;
linear or branched alkyl with 1 to 6 carbon atoms;
benzyl;
aliphatic acyl, that is $COR_2$ wherein $R_2$ is a linear or branched alkyl with 1 to 6 carbon atoms;
hemicaryl of a dicarboxylic acid; and where $R_1$ is:
—SH or an acylthio group that is —$SCOR_3$, where $R_3$ is a lower alkyl.

2. A compound according to claim 1, wherein R is acetyl or hemisuccinoyl, and $R_1$ is —SH or an acylthio group, that is —$SCOR_3$, wherein $R_3$ is a lower alkyl.

3. A compound according to claim 1, wherein $R_1$ is an acetylthio group, that is —$SCOOCH_3$.

4. A compound of formula:

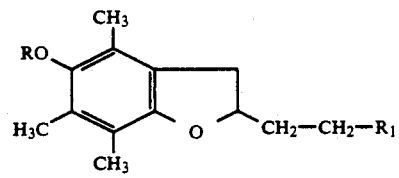

wherein R is hemisuccinoyl and $R_1$ is acetylthio.

5. A pharmaceutical composition having antioxidizing/radical-scavenging and mucoregulating activity, comprising a compound of claim 1 and a pharmaceutically acceptable inert diluent.

6. A pharmaceutical composition according to claim 5, in the form of solutions, syrups, tablets, capsules, salves and suppositories.

* * * * *